US010025272B2

(12) United States Patent
Falter et al.

(10) Patent No.: US 10,025,272 B2
(45) Date of Patent: Jul. 17, 2018

(54) ULTRASONIC HOLOGRAPHY IMAGING SYSTEM AND METHOD

(71) Applicant: General Electric Company, Schenectady, NY (US)

(72) Inventors: Stephan Falter, Simmerath (DE); Dieter Lingenberg, Huerth (DE)

(*) Notice: Subject to any disclaimer, the term of this patent is extended or adjusted under 35 U.S.C. 154(b) by 368 days.

(21) Appl. No.: 13/750,582

(22) Filed: Jan. 25, 2013

(65) Prior Publication Data
US 2014/0211588 A1  Jul. 31, 2014

(51) Int. Cl.
*G01S 15/00* (2006.01)
*G03H 3/00* (2006.01)
*G01S 15/89* (2006.01)
*G01N 29/06* (2006.01)

(52) U.S. Cl.
CPC .......... *G03H 3/00* (2013.01); *G01N 29/0663* (2013.01); *G01S 15/897* (2013.01); *G01S 15/8993* (2013.01); *G01N 2291/0423* (2013.01); *G01N 2291/0427* (2013.01); *G01N 2291/106* (2013.01); *G01S 15/8925* (2013.01); *G01S 15/8977* (2013.01); *Y10T 29/49005* (2015.01)

(58) Field of Classification Search
USPC .......................................................... 367/8
See application file for complete search history.

(56) References Cited

U.S. PATENT DOCUMENTS 3,655,258 A  4/1972  Hildebrand
3,832,888 A  9/1974  Langlois
3,911,729 A  10/1975  Collins
3,964,052 A  6/1976  Langlois
3,983,529 A  9/1976  Langlois
4,021,771 A  5/1977  Collins et al.
4,165,647 A * 8/1979  Collins ............................ 73/603

(Continued)

FOREIGN PATENT DOCUMENTS

CN  1196483 A  10/1998
CN  1636151 A  7/2005

(Continued)

OTHER PUBLICATIONS

Thomas, Gabriel, et al., "Frequency Compounding of Synthetic Aperture Ultrasound Imagery using Multiscale Products", Instrumentation and Measurement Technology Conference (12MTC), IEEE, May 3, 2010, pp. 702-705, Piscataway, NJ, USA.

(Continued)

*Primary Examiner* — James R Hulka
(74) *Attorney, Agent, or Firm* — Mintz Levin Cohn Ferris Glovsky and Popeo, P.C.

(57) ABSTRACT

An ultrasonic holography imaging system and method are provided. The ultrasonic holography imaging system includes an ultrasonic transducer array coupled to an analog processing section. The analog processing section is coupled to a digital processing section. The digital processing section generates digital signals to be converted by the analog processing section into analog signals that are transmitted to individual transceiver elements within the ultrasonic transducer array to cause separate ones of the individual transceiver elements to emit ultrasonic waveforms that are differentiated from each other by one or more parameters, including amplitude, frequency, and phase or modulation thereof.

20 Claims, 6 Drawing Sheets

(56) References Cited

U.S. PATENT DOCUMENTS

| | | | |
|---|---|---|---|
| 4,222,273 A * | 9/1980 | Takahashi | G01N 29/0663 73/603 |
| 4,222,274 A | 9/1980 | Johnson | |
| 4,653,000 A | 3/1987 | Matsumoto | |
| 5,212,571 A * | 5/1993 | Garlick | G03H 3/00 359/9 |
| 6,023,660 A | 2/2000 | Dory | |
| 6,590,830 B1 | 7/2003 | Garlick et al. | |
| 6,757,215 B2 | 6/2004 | Garlick et al. | |
| 6,816,291 B2 * | 11/2004 | Tanaka | G03H 1/0248 359/22 |
| 6,831,874 B2 | 12/2004 | Garlick et al. | |
| 6,900,914 B1 * | 5/2005 | Tanaka | G03H 1/0248 359/10 |
| 7,259,897 B2 | 8/2007 | Garlick et al. | |
| 7,581,444 B2 | 9/2009 | Maurer et al. | |
| 7,987,724 B2 | 8/2011 | Takada | |
| 8,226,561 B2 | 7/2012 | McLaughlin et al. | |
| 8,235,902 B2 | 8/2012 | Chen et al. | |
| 2002/0118600 A1 | 8/2002 | Garlick et al. | |
| 2003/0039000 A1 * | 2/2003 | Tanaka | G03H 1/0248 359/22 |
| 2003/0097066 A1 | 5/2003 | Shelby et al. | |
| 2003/0158482 A1 | 8/2003 | Poland et al. | |
| 2004/0037164 A1 * | 2/2004 | Garlick | G01N 29/075 367/8 |
| 2005/0203415 A1 | 9/2005 | Garlick et al. | |
| 2006/0195273 A1 * | 8/2006 | Maurer et al. | 702/39 |
| 2009/0036775 A1 * | 2/2009 | Ikuma | A61B 8/12 600/443 |
| 2009/0069677 A1 * | 3/2009 | Chen et al. | 600/439 |
| 2009/0241675 A1 * | 10/2009 | Takada | 73/641 |
| 2010/0268082 A1 * | 10/2010 | McLaughlin et al. | 600/443 |
| 2011/0046935 A1 * | 2/2011 | Sugaya | G06F 19/3437 703/11 |
| 2011/0144500 A1 * | 6/2011 | Nihei | A61L 38/14 600/443 |

FOREIGN PATENT DOCUMENTS

| | | |
|---|---|---|
| DE | 2923687 A1 | 4/1981 |
| EP | 0005593 A1 | 11/1979 |
| EP | 0872742 B1 | 7/2001 |
| EP | 0825453 B1 | 8/2001 |
| EP | 1965208 A1 | 9/2008 |
| EP | 1597607 B1 | 7/2010 |
| JP | 6358484 A | 3/1988 |
| JP | 11235339 A | 8/1999 |
| JP | 2004117275 A | 4/2004 |
| JP | 2012196302 | 10/2012 |
| KR | 1144692 B1 | 5/2012 |
| WO | 03029808 A1 | 4/2003 |
| WO | 2004074864 A1 | 9/2004 |
| WO | 2005059591 | 6/2005 |

OTHER PUBLICATIONS

Yoshizumi, Natsuki, et al., "Multiple-Frequency Ultrasonic Imaging by Transmitting Pulsed Waves of Two Frequencies", Journal of Medical Ultrasonics, Jun. 17, 2009, pp. 53-60, vol. No. 36, Issue No. 2.

EP Search Report and Written Opinion dated May 27, 2014 in connection with corresponding EP Patent Application No. 14152003.1.

Machine translation and Chinese Office Action issued in connection with corresponding CN Application No. 201410033869.6 dated Jun. 2, 2017.

Japanese Office Action for JP Application No. 2014011313 dated Nov. 7, 2017; 7 Pages.

* cited by examiner

ULTRASONIC HOLOGRAPHY IMAGING SYSTEM AND METHOD

BACKGROUND OF THE INVENTION

The present disclosure relates generally to ultrasonic holography imaging systems for use in generating three-dimensional images by acoustic waves, and more particularly, to methods for imaging features within physical items using ultrasonic holography.

In systems for use, for example, in non-destructive testing of physical items, non-invasive techniques are often required in order to determine conditions within an interior of a physical item. Ultrasonic vibrations have the capability of penetrating into and reflecting out of, or passing through, a solid physical item. By analyzing alterations in the patterns and frequencies of the ultrasonic vibrations after they have passed through a physical item, a visual image of the physical item, including features within the physical item, can be generated.

Specifically, an ultrasonic generator causes an emitter element (transducer) to produce a directed sound field that propagates into a physical item to be tested. In some imaging systems, reflections of defects within the physical item, for example, are directed at least in part, back to a receiver. The emitter and receiver elements may be separate components within an array, or may be the same individual component functioning both as an emitter and a receiver (referred to as a "transceiver"); similar to the manner in which a speaker can also function as a microphone. The sound field generates electrical impulses within the receiver. The electrical impulses are converted into data, which is processed to create a visual image. Phased-array transducers are used to provide a series of separate sound impulses ("tone bursts") that can be separated in time from each other, to enable a directed sound field to be generated. For example, if an array of individual ultrasonic transducers is actuated so that tone bursts are emitted that are spaced apart in time a fixed amount between adjacent emitters, an angled planar sound wave can be generated.

Existing phased-array transducers produce sound fields that have shapes that are derived from by the configuration of the transducer array, which is typically planar or a simple curved shape. Furthermore, existing ultrasonic generators produce only shifts in phase between waves emanated from separate emitters. This limits the capacity for existing ultrasonic holography imaging systems to produce complex forms of wave fronts. Accordingly, it would be desirable to provide an ultrasonic holography imaging system that is capable of producing detailed sound fields that are not constrained by the configuration of the transducer array, so as to provide enhanced imaging that is capable of addressing the shape and configuration of the physical item being imaged.

BRIEF DESCRIPTION OF THE INVENTION

In an aspect, an ultrasonic holography system is provided. The ultrasonic holography system includes an ultrasonic transducer array having a predefined shape, the ultrasonic transducer array including a plurality of transceiver elements configured to emit a plurality of ultrasonic waveforms toward a physical item, and receive a plurality of return ultrasonic waveforms reflected from the physical item. The ultrasonic holography system also includes a processor system coupled to the ultrasonic transducer array. The processor system is configured to generate a plurality of outgoing analog transceiver driving signals configured to cause the ultrasonic transducer array to emit the plurality of ultrasonic waveforms, wherein at least two of the plurality of ultrasonic waveforms are differentiated from each other through variation of at least one of amplitude, frequency, and phase, or modulation thereof, to form an acoustic image. The processor system is further configured to receive a plurality of incoming analog waveform signals, generated by the ultrasonic transducer array, the incoming analog waveform signals representative of at least a portion of the plurality of return ultrasonic waveforms. The processor system is further configured to construct a virtual image, using the plurality of incoming analog waveform signals, the virtual image corresponding to at least a portion of an internal region of the physical item.

In another aspect, a method for assembling an ultrasonic holography system is provided. The method includes coupling a plurality of ultrasonic transceiver elements to form an ultrasonic transducer array having a predefined shape, the plurality of transceiver elements configured to emit a plurality of ultrasonic waveforms toward a physical item, and receive a plurality of return ultrasonic waveforms reflected from the physical item. The method also includes coupling a processor system to the ultrasonic transducer array. The processor system is configured to generate a plurality of outgoing analog transceiver driving signals configured to cause the ultrasonic transducer array to emit the plurality of ultrasonic waveforms, wherein at least two of the plurality of ultrasonic waveforms are differentiated from each other through variation of at least one of amplitude, frequency, phase, or modulation thereof, to form an acoustic image. The processor system is also configured to receive a plurality of incoming analog waveform signals, generated by the ultrasonic transducer array, the incoming analog waveform signals representative of at least a portion of the plurality of return ultrasonic waveforms. The processor system is also configured to construct a virtual image, using the plurality of incoming analog waveform signals, the virtual image corresponding to at least a portion of an internal region of the physical item.

In another aspect, a method for imaging a physical item using ultrasonic holographic imaging is provided. The method is implemented using a processor system including a processing section coupled to a memory device. The method includes defining an image structure using data stored in the memory device, the data representing a geometry of the physical item. The method further includes configuring an ultrasonic transducer array, the ultrasonic transducer array comprising a plurality of ultrasonic transceiver elements. The method further includes coupling the ultrasonic transducer array to the processing section and the memory device. The method further includes storing, in the memory device, instructions executable by the processor system to cause the ultrasonic transducer array to emit a plurality of ultrasonic waveforms representative of the defined image structure, wherein at least two of the of ultrasonic waveforms are differentiated from each other through variation of at least one of amplitude, frequency, and phase, or modulation thereof, to form an acoustic image.

DETAILED DESCRIPTION OF THE INVENTION

Although specific features of various embodiments of the invention may be shown in some drawings and not in others, this is for convenience only. In accordance with the principles of the invention, any feature of a drawing may be referenced and/or claimed in combination with any feature of any other drawing.

The methods and systems described herein may be implemented using computer programming or engineering techniques including computer software, firmware, hardware or any combination or subset thereof, wherein the technical effects may be achieved by performing at least one of the following steps: a) defining an image structure using data stored in a memory device, the data representing a geometry of a physical item; b) configuring an ultrasonic transducer array, the ultrasonic transducer array comprising a plurality of ultrasonic transceiver elements; c) coupling the ultrasonic transducer array to a processing section and the memory device; d) storing, in the memory device, instructions executable by the processing section to cause the ultrasonic transducer array to emit a plurality of ultrasonic waveforms representative of the defined image structure, wherein at least two of the ultrasonic waveforms are differentiated from each other through variation of at least one of amplitude, frequency, and phase; e) emitting into a physical item, with the ultrasonic transducer array, a plurality of ultrasonic waveforms representative of the defined image structure to form an acoustic image inside the physical item; f) receiving, with the ultrasonic transducer array a plurality of ultrasonic waveforms reflected from the physical item; g) processing the plurality of reflected ultrasonic waveforms to produce a plurality of digital A-Scans; and h) evaluating the plurality of digital A-scans.

Figure 1:
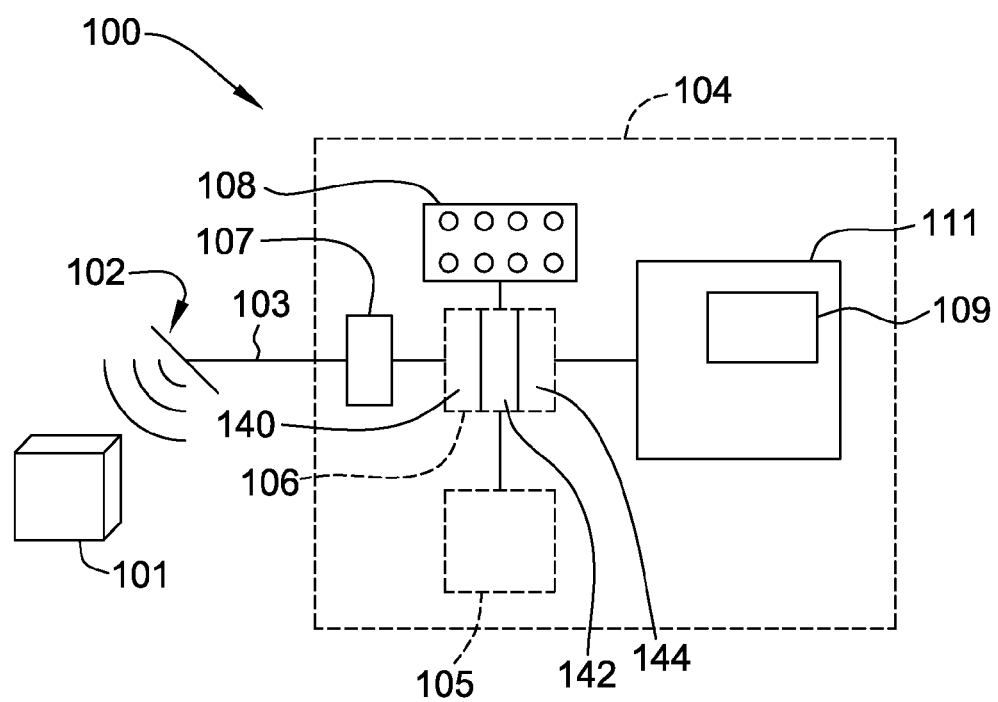
FIG. 1 is a schematic illustration of an environment in which an exemplary ultrasonic holography system is used.

FIG. 1 is a schematic illustration of an exemplary ultrasonic holography imaging system 100, for use in performing ultrasonic holographic imaging of a physical item 101. System 100 includes an ultrasonic transducer array 102, coupled to a processor system 104 via a connection 103. Connection 103 may be any suitable connection device(s) sufficient to enable system 100 to function as described herein, including a hard-wired arrangement, a fiber-optic transmission arrangement, or a combination thereof. In the exemplary embodiment, ultrasonic transducer array 102 emits ultrasonic tone pulses and also receives ultrasonic waves that are reflected off of physical item 101. More specifically, ultrasonic waves emitted by transducer array 102 are, in some embodiments, configured to penetrate into physical item 101, and reflect off of structures within physical item 101, such as areas of decreased density (which may be suggestive of corrosion), or other flaws within physical item 101. In the exemplary embodiment, ultrasonic transducer array 102 is a rectangular array (m times n units) of individual ultrasonic transceiver elements 110 (illustrated in FIG. 2). In the exemplary embodiment, each ultrasonic transceiver element is a piezoelectric transceiver element. In alternative embodiments, other types of ultrasonic transceiver elements, such as electromagnetic acoustic transducers (""EMATs") or capacitive micromachined ultrasonic transducers ("CMUTs"), known to those skilled in the art may be used to enable system 100 to function as described. Each ultrasonic transceiver element 110 is configured to transmit and receive ultrasonic waveforms. Processor system 104 includes an analog processing section 107 coupled to a digital processing section 106. Digital processing section 106 is coupled to a memory device (database) 105, and a control panel 108 (or keyboard or other user input device or devices). Digital processing section 106 provides signals to display 111 to generate a display image 109.

As used herein, the term "processor" is not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

In the exemplary embodiment, as described herein, several series of "shots" of physical item 101 are taken while imaging physical item 101. Accordingly, ultrasonic transducer array 102 is moved to a first position relative to physical item 101, and one or more series of ultrasonic pulses are emitted towards physical item 101, reflections of those ultrasonic pulses are received by ultrasonic transducer array 102, and data corresponding to the emitted pulses and corresponding received reflections is stored and later processed. Ultrasonic transducer array 102 is then moved to another position relative to physical item 101, and another series of "shots" is taken. The number of shots taken and positions used is dependent upon the configuration of physical item 101 and the type of image that is being acquired (imaging to detect flaws, etc.). In the exemplary embodiment, ultrasonic transducer array 102 can be caused by digital processing section 106 to emit ultrasonic waveforms that, upon contact with physical item 101, in turn cause a variety of different waveforms to propagate through physical item 101, including Rayleigh waves (used, for example, in analyzing determining mechanical and structural properties of a material, such as cracking), that are waves confined to the surface of an object; Lamb waves (which are typically used to find and characterize individual flaws in an object being tested), that are waves that penetrate into the interior of an object; or creep waves which typically serve to have access to test areas hidden below other parts of a test object, e.g. welds or solders.

Figure 2A:
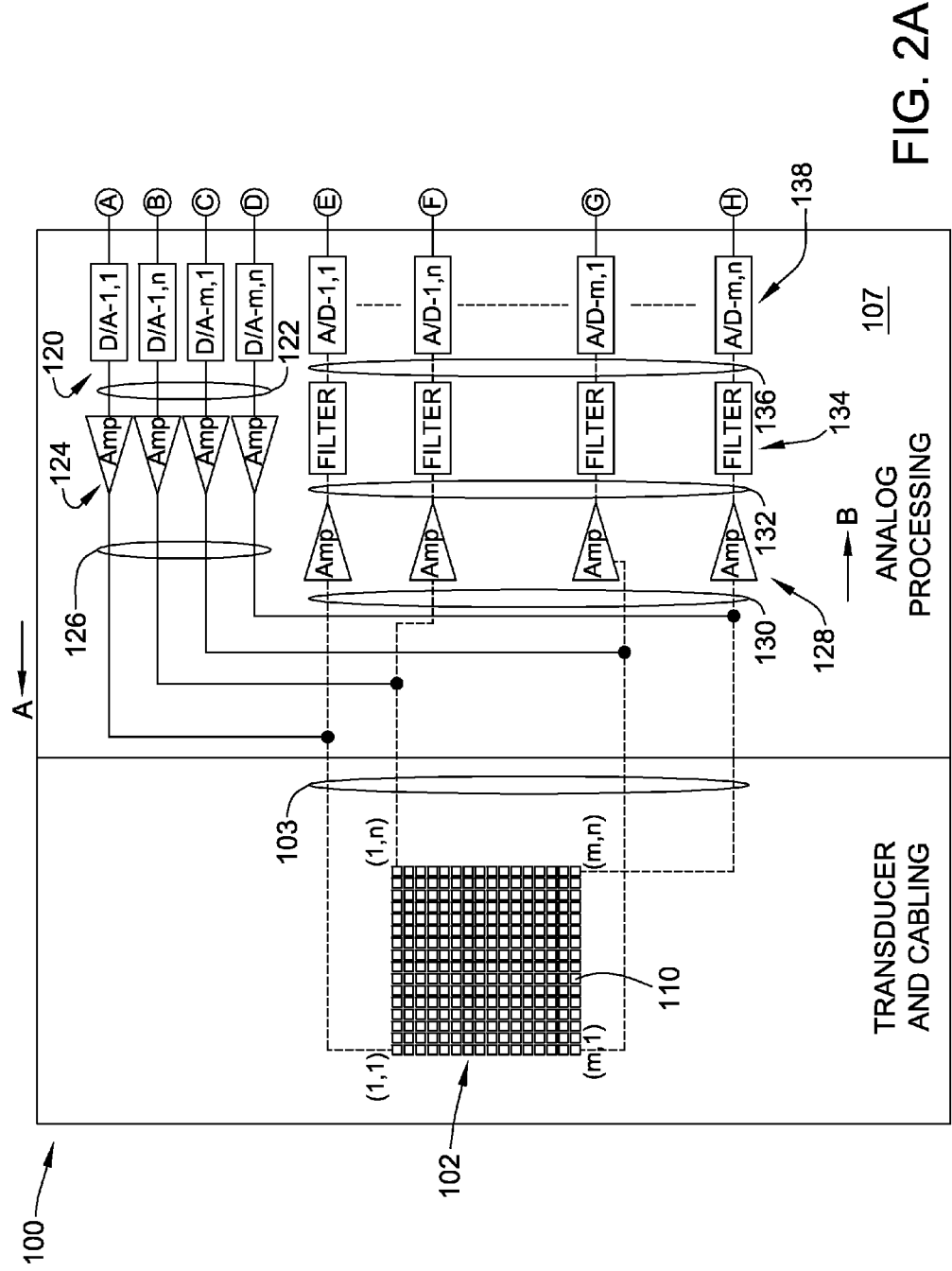
FIG. 2A is a portion of a circuit diagram illustrating sensor and hardware portions of an exemplary ultrasonic holography system.
Figure 2B:
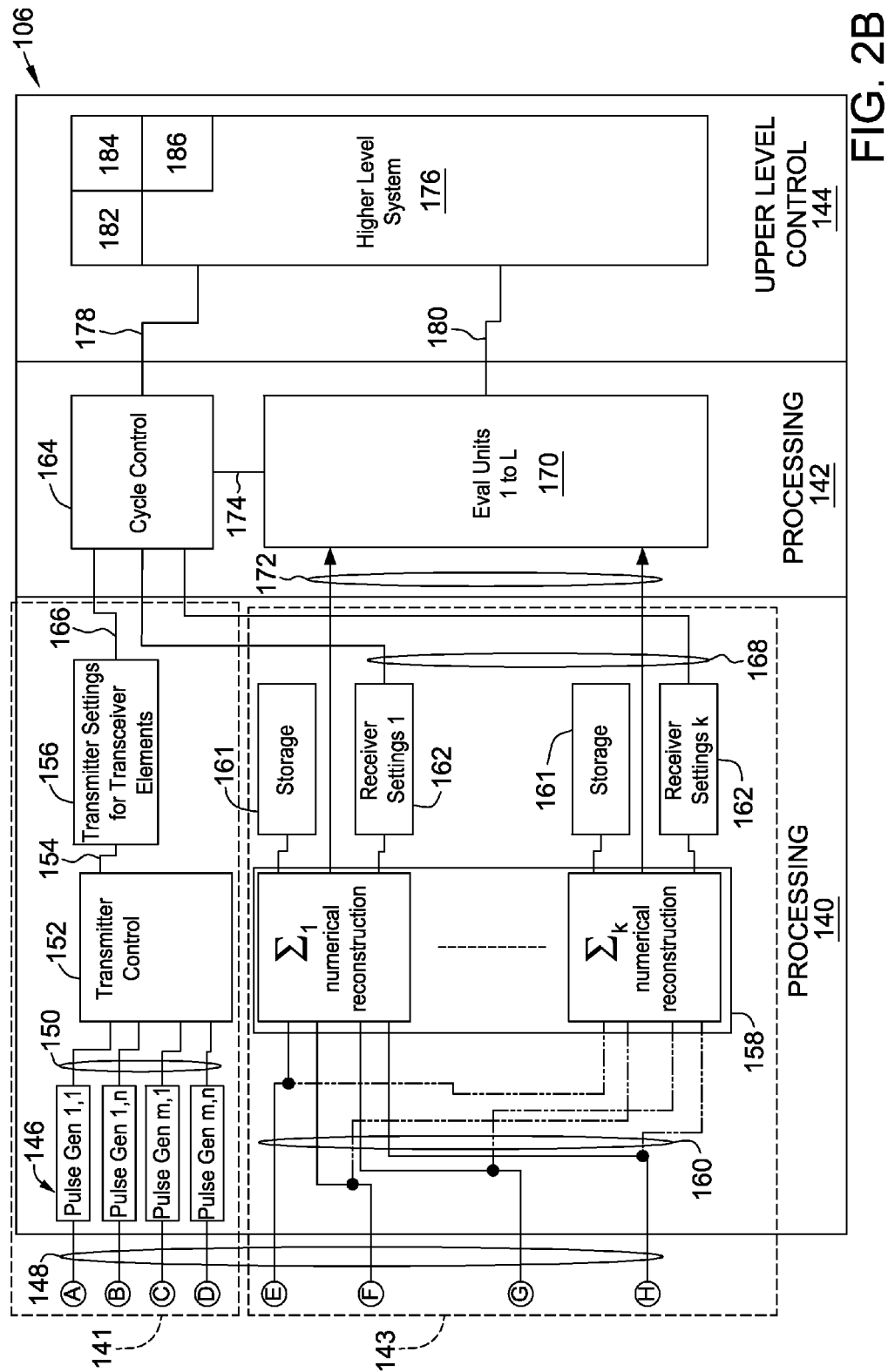
FIG. 2B is a further portion of a circuit diagram, illustrating processor portions of an exemplary ultrasonic holography system.

FIGS. 2A and 2B together form a circuit diagram illustrating exemplary ultrasonic holography imaging system 100. Specifically, FIG. 2A is a portion of a circuit diagram illustrating ultrasonic transducer array 102 and analog processing section 107 of ultrasonic holography imaging system 100, and FIG. 2B is a further portion of a circuit diagram, illustrating digital processing section 106 of ultrasonic holography imaging system 100. Analog processing section 107 performs preprocessing of signals transmitted between ultrasonic transducer array 102 and digital processing section 106. Specifically, analog processing section 107 converts digital signals generated by digital processing section 106 and transmitted to ultrasonic transducer array 102 (as indicated by an arrow A pointing to the left) into analog signals that stimulate selected ones of ultrasonic transceiver elements 110. Analog processing section 107 also converts analog signals transmitted from ultrasonic transceiver elements 110, that represent ultrasonic waves reflected from physical item 101 and received by ultrasonic transceiver elements 110, into digital signals and transmits those digital signals to digital processing section 106 (as indicated by an arrow B pointing to the right). Analog processing section 107 includes a plurality of digital-to-analog ("D/A") converters 120 coupled via a plurality of connections 122 to a corresponding plurality of amplifiers 124. Although only four (4) sets of D/A converters 120 and corresponding amplifiers 124 are illustrated, it is understood that in the exemplary embodiment, a D/A converter 120 and corresponding amplifier 124 is provided for, and coupled to, each of ultrasonic transceiver elements 110. Amplifiers 124 are coupled, via a plurality of connections 126, to corresponding ones of connections 103, and in turn, to corresponding ones of ultrasonic transceiver elements 110 of ultrasonic transducer array 102. As described above, although only four (4) connections 103 are illustrated in FIG. 2A, in the exemplary embodiment, a separate connection 103 couples each one of ultrasonic transceiver elements 110 to a corresponding one of amplifiers 124.

Analog processing section 107 also includes a plurality of amplifiers 128 that are coupled, via connections 130, to connections 103, and in turn to respective ones of ultrasonic transceiver elements 110 of ultrasonic transducer array 102. That is, although only four (4) amplifiers 128 are illustrated in FIG. 2A, it is understood that in the exemplary embodiment, there is an amplifier 128 coupled to each of ultrasonic transceiver elements 110. Each of amplifiers 128 is coupled, via one of connections 132 to a respective one of a plurality of filters 134. Each of filters 134 is coupled, via one of connections 136, to a corresponding one of a plurality of analog-to-digital ("A/D") converters 138. Filters 134 may be any suitable electronic signal filters necessary to enable system 100 to function as described herein. A/D converters 138 convert into digital signals, electronic waveforms received by ultrasonic transceiver elements 110 and transmitted to A/D converters 138.

Analog processing section 107 is coupled to digital processing section 106 (illustrated in FIG. 2B). Digital processing section 106 includes, in the exemplary embodiment, a primary digital processing section 140, a secondary digital processing section 142, and an upper level control section 144. Primary digital processing section 140 includes a waveform shaping section 141, and an image reconstruction and evaluation section 143.

In waveform shaping section 141, a plurality of pulse generators 146 are coupled, via a plurality of connections 148, to corresponding ones of a plurality of D/A converters 120 (shown in FIG. 2A). Pulse generators 146 are coupled, via a plurality of connections 150, to a transmitter control unit 152. Transmitter control unit 152 regulates characteristics of tone burst pulses, by varying factors such as amplitude, frequency, phase, amplitude modulation, phase modulation, and frequency modulation, with respect to each transceiver element 110. Transmitter control unit 152 is coupled, via connection 154, to a transmitter settings unit 156. Transmitter settings unit 156 stores and monitors settings for ultrasonic transceiver elements 110 required to generate a specifically shaped ultrasonic pulse field, including selection of timing, magnitude, amplitude and frequency and modulations of any thereof, for each pulse emitted by each ultrasonic transceiver element 110. The ultrasonic pulses propagate into the material area, where they interfere with each other. The result of this interference process is an acoustic image created inside the material.

In image reconstruction and evaluation section 143, a summation unit 158 is coupled to each of A/D converters 138 via a plurality of connections 160. Each A/D converter 138 produces a single element digitized signal (also referred to as an "A-scan"). In order to perform a numerical reconstruction of the reflected sound field embodied in the individual A-scans, summation unit 158 performs a summation process (also referred to as "numerical reconstruction") on the data signals received from each of the piezoelectric units, to produce a virtual A-scan of the complete physical item 101. Summation unit 158 is, in an exemplary embodiment, configured as a plurality of field-programmable gate arrays ("FPGAs") (not shown) coupled to A/D converters 138. In alternative embodiments, other components may be used in place of FPGAs, such as application-specific integrated circuits ("ASICs"), which enable system 100 to function as described.

The summation process, in the exemplary embodiment, may be briefly described as follows Summation unit 158 sums the single element A-scans pointwise in time (using time-steps (t0, t1, t2, . . . tFinal)). Accordingly, if the A-Scans are AScan1(t0,t1,t2, . . . tn), Ascan2(t0,t1,t2, . . . tn), etc., then $$A\text{-ScanSum}(t0)=A\text{Scan}1(t0+Dt(1))+A\text{Scan}2(t0+Dt(m))+\ldots$$

$$A\text{-ScanSum}(t1)=A\text{Scan}1(t1+Dt(2))+A\text{Scan}2(t1+Dt(m+1))+\ldots \text{ through}$$

$$A\text{-ScanSum}(t\text{Final})=A\text{Scan}1(t\text{Final}+Dt(n))+A\text{Scan}2(t\text{Final}+Dt(m+n))+\ldots$$

which results in a single summed A-Scan. The summation process is continued, during which various factors may be varied, including the contributing number of single element A-scans, a predefined time interval for a length of the tone bursts, and a time delay between tone bursts of adjacent piezoelectric elements Dt(x). Selection of factors to be varied is accomplished using ultrasonic testing and/or beamforming techniques known to those skilled in the art.

Image reconstruction and evaluation section 143 further includes a plurality of storage elements 161, for storing incoming unprocessed raw digital signals transmitted from A/D converters 138, to enable multiple evaluations to be performed using a single set of incoming data, for purposes of improving quality of subsequently processed digital signals.

Image reconstruction and evaluation section 143 serves several functions. One function is to translate raw analog data signals transmitted from ultrasonic transducer array 102, and preliminarily processed by analog processing section 107 into a series of A-ScanSums. The A-ScanSums serve as a basis for ultrasonic test evaluation, performed in secondary digital processing section 142, specifically in evaluation units 1-L. Collectively, the series of A-ScanSums form a raw virtual image of physical item 101. Image reconstruction and evaluation section 143 processes the raw virtual image to remove noise by optimizing echoes created by features within physical item 101 that might serve as reflectors of the ultrasonic waves being emitted into physical item 101. Such reflectors may represent flaws within physical item 101. The functions ascribed to secondary digital processing section 142 may be performed by any suitable processor devices configured to enable secondary digital processing section 142 to function as described herein.

As in analog processing section 107 and primary digital processing section 140, secondary digital processing section 142 includes functions related to the creation of the waveforms ultrasonic transducer array 102 transmits into physical item 101, as well as functions related to processing of waveforms reflected from physical item 101 and received by ultrasonic transducer array 102. A cycle control unit 164 is coupled to transmitter settings unit 156 via a connection 166, and coupled to summation unit 158 via a plurality of connections 168. Evaluation units (1-k) 170 are coupled via connections 172 to summation unit 158, and to cycle control unit 164 via a connection 174.

Cycle control unit 164 is coupled to a higher level processing unit 176, located in upper level control section 144 via a connection 174. Evaluation units (1-k) 170 are coupled to higher level processing unit 176 via connection(s) 180.

Cycle control unit 164 is configured to regulate operations of system 100. Specifically, system 100 functions in a series of cycles. Each cycle includes a set of specifically configured ultrasonic pulses (or "tone bursts") emitted from each of ultrasonic transceiver elements 110, followed by a pause, followed by the receipt of a series of reflected sound waves by each of ultrasonic transceiver elements 110, which are, in turn, converted by analog processing section 107 into a series of digital signals to be processed by digital processing section 106. Data corresponding to each set of ultrasonic pulses is stored in cycle control unit 164 in the form of a table (a "cycle table") that defines various characteristics of each series of pulses, such as the number of "shots" to be taken, the directions in which each shot is taken, the number of positions around physical item 101 that shots are to be taken, etc.

Evaluation units 170 perform ultrasonic test evaluations on raw virtual images created and stored in summation unit 158, or results deduced thereof, according to techniques known to those skilled in the art. Each raw virtual image represents a plurality of ultrasonic reflections of ultrasonic "shots" taken at a predefined series of time intervals and a plurality of positions about physical item 101, to generate a three-dimensional ultrasonic "field." An additional function of evaluation units 170 is correlation of data acquired during testing with positions on physical item 101. Specifically, position encoders (not shown) are coupled to ultrasonic transducer array 102 and to digital processing section 106, to report and record positions of ultrasonic transducer array 102 relative to physical item 101. Analysis of the ultrasonic field includes, for example, selection of a segment or "slice" in time (also referred to as a "gate"). The gate is analyzed to determine the largest sound wave amplitude within the gate, and a measured time in flight associated with that amplitude. As used herein, "time in flight" refers to the amount of time required for a sound wave to travel through the physical item 101. The selected amplitude is compared to predefined reference amplitude, and the measured time of flight is compared to a predefined reference time of flight. If the selected amplitude exceeds the value of the reference amplitude, then a defect is deemed to be present at a physical location within physical item 101 that is associated with the selected gate. For example, a measured time of flight associated with a selected gate that registers below the predefined reference time of flight, may be indicative that the strength of the material in physical item 101, at the associated location may be too low, as may be associated with internal corrosion at that location. Alternatively, for situations in which corrosion is present on an external surface of item 101, the measured time of flight may be greater than the predefined reference time of flight.

Higher level processing unit 176 includes PCs, desktop systems, stand-alone CPUs, and/or other systems that use the evaluations generated by evaluation units 170 to record data regarding physical item 101, to stimulate a process control, or generate a visualization for a user, for example. In addition, higher level processing unit functions as a command center for system 100, wherein a user inputs instructions and data, such as data regarding physical item 101, and parameters for causing waveform shaping section 141 to create signals that will induce, in physical item 101 the desired acoustic image tailored to cause potential reflectors in the material to optimally reflect acoustic waves for reception by system 100 and subsequent processing of those acoustic waves. In other embodiments, specific types of acoustic waves, as e.g. Rayleigh Waves or Lamb Waves, are excited within item 101. Higher level processing unit 176 also includes display devices 182 (including two- and three-dimensional visual displays), user input devices 184 (keyboards, touchscreens, etc.), communications interfaces 186, and other equipment associated with ultrasonic materials analysis as known to those skilled in the art. A user provides input to cycle control unit 164 via input devices (not shown) associated with higher level processing unit 176 in upper level control section 144. In the exemplary embodiment, the functions of upper level control section 144 are performed on a computer, which may be of any suitable configuration sufficient to enable system 100 to function as described herein. Higher level processing unit 176 receives processed digital data from secondary digital processing section 142, and translates the data into visual displays that may be configured by a user through a suitable user interface programmed into higher level processing unit 176, including functions such as providing correct "false color" for two-dimensional displays, three-dimensional displays, and creation of charts, etc., In addition, higher level processing unit 176 performs additional evaluation functions that are enabled after a complete testing of physical item 101 has been performed, such as the creation of analytical reports, etc.

Figure 3A:
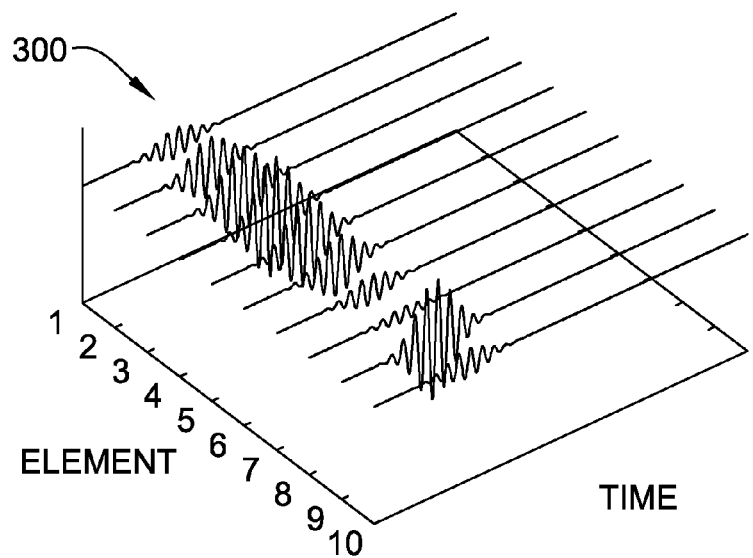
FIG. 3A is a perspective graphic representation of an exemplary series of waveforms used in an exemplary ultrasonic holography imaging system.
Figure 3B:
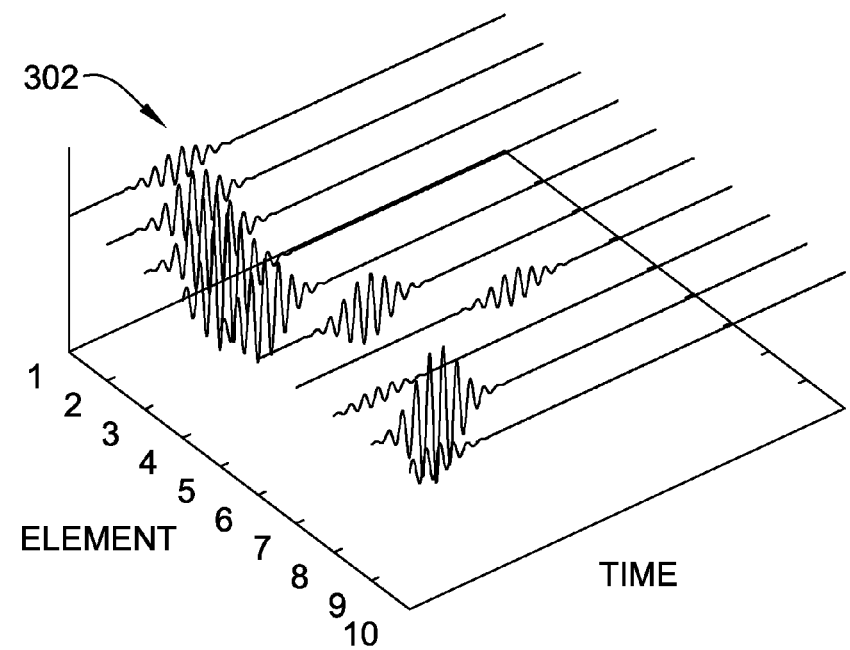
FIG. 3B is another perspective graphic representation of another exemplary series of waveforms used in an exemplary ultrasonic holography imaging system.
Figure 3C:
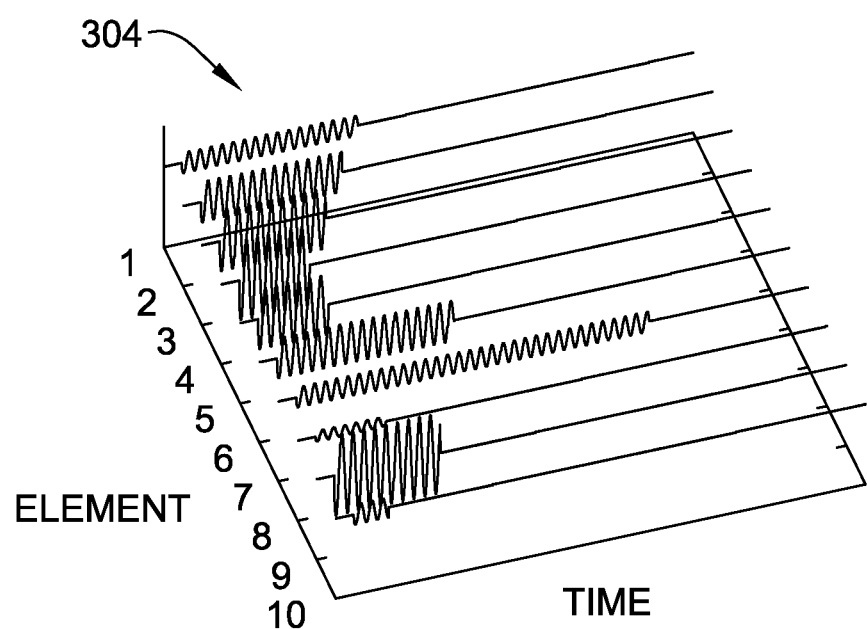
FIG. 3C is another perspective graphic representation of another exemplary series of waveforms used in an exemplary ultrasonic holography imaging system.

In the exemplary embodiment, signals generated by digital processing section 106 cause ultrasonic transducer array 102 to emit ultrasonic tone bursts that are non-homogeneous across a width and breadth of ultrasonic transducer array 102. FIGS. 3A-3C illustrate different configurations of waveforms, and wave fronts, that are provided by the exemplary system 100. FIG. 3A is a perspective graphic view of a series of waveforms 300 illustrating a first mode of variation of tone bursts. For simplicity of illustration, tone bursts from a single row of ultrasonic transceiver elements 110 are illustrated. Specifically, waveforms 300 represent tone bursts that vary in amplitude, but are constant in duration and time of emission. FIG. 3B illustrates a second mode of variation of tone bursts in which a plurality of waveforms 302 represent tone bursts that vary in amplitude, and in time of emission ("time shift"), but are constant in duration. FIG. 3C illustrates a series of waveforms 304 that represent a series of tone bursts that time shifted, and variable in amplitude and duration.

Figure 4:
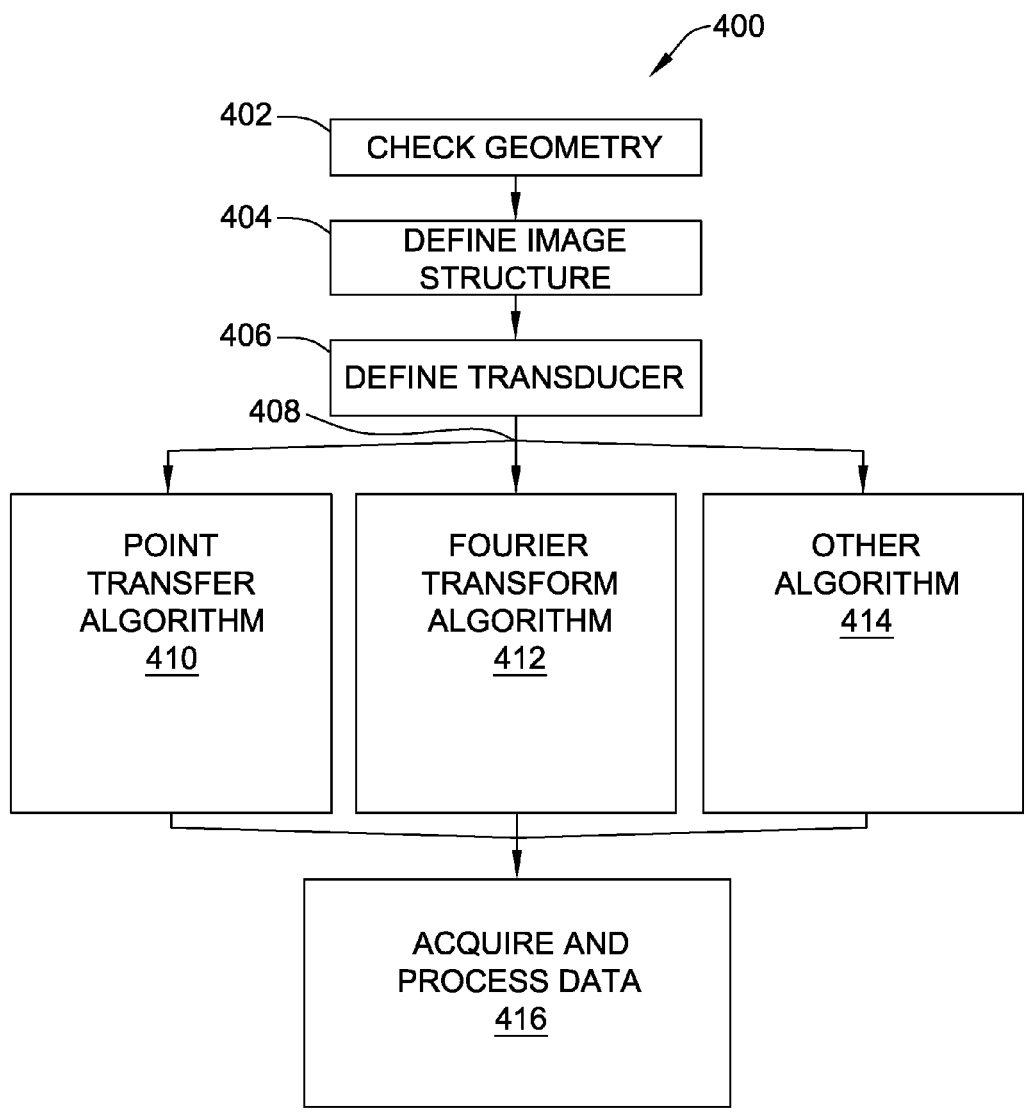
FIG. 4 is a flowchart illustrating an exemplary method for imaging a physical item using ultrasonic holography.

FIG. 4 illustrates an exemplary method 400 for performing imaging through ultrasonic holography. First, the geometry of physical item 101 that is to be inspected is measured and the corresponding data is stored 402 in system 100. Accordingly, areas of physical item 101 that are known to be historically susceptible to defects in similar physical items are identified, enabling a desired image physical item to be defined 404. Once the geometry of the physical item 101 to be inspected and the desired image structure are known, a configuration of a transducer to obtain the desired acoustic image is defined 406. For example, a size of an array of piezoelectric elements is selected, an appropriate tone burst pulse frequency is selected, and individual piezoelectric element size and geometry is selected. While in the exemplary embodiment, piezoelectric ultrasonic elements are used as the emitter/receivers for ultrasonic waves, any suitable ultrasonic emitter/receiver type may be used that enables system 100 to function as described herein. An appropriate data processing algorithm is selected 408, for use in converting the image structure defined at 404 into a series of tone bursts having predefined individual configurations, with respect to each ultrasonic transceiver element 110. Several available data processing algorithms, adapted from optical imaging systems known to those skilled in the art, may be used, including a point transfer algorithm 410, a Fourier Transform algorithm 412, or other existing algorithms 414 for performing digital holography.

The selected data processing algorithm is used to transform the defined image structure into instructions to be transmitted to waveform shaping section 141. For example, use of a point transfer algorithm 410 involves transforming a defined 404 image structure into an array of points in space, defining grayscale values for each point in the array, calculating a desired amplitude and phase for waveforms to be emitted that will impinge upon each point in the array, and providing coherent addition of contributions from each image point to determine the amplitude and phase of each tone burst from each element. The result of use of point transfer algorithm 410 results in the definition of an interference pattern that ultrasonic transducer array 102 will create upon emission of the defined series of tone bursts. Use of a Fourier Transform algorithm 412 transforming a defined 404 image structure into an array of points in space, and calculating a Fourier transform of the defined image, using optical Fourier propagation to transfer the Fourier transform of the defined image to ultrasonic transducer array 102. The result of use of point transfer algorithm 410 or Fourier Transfer algorithm 412 results in the definition of an interference pattern that ultrasonic transducer array 102 will create upon emission of the defined series of tone bursts, which then interferes to the real acoustic image.

After selection 408 of a desired algorithm for processing data to be acquired, actual data acquisition 416 occurs. During data acquisition 416, one or more ultrasonic pulses are emitted by ultrasonic transducer array 102, with tone bursts emitted from different ones of ultrasonic transceiver elements 110 varying in amplitude, duration, and/or time shift, as appropriate for the geometry of physical item 101 being imaged and the predefined desired image structure. Reflected ultrasonic waves are received by ultrasonic transceiver elements 110, and raw waveform signals are stored in storage elements 161. The raw signals are amplified and pre-processed in analog processing section 107 of system 100 to produce A-scans, as described. Once generated, A-scans may be evaluated using known ultrasonic imaging techniques, for example to develop higher level visualizations, such as B-scans. As used herein, "B-scans" refers to a fully-developed, color scale three-dimensional image of an object. Data contained in A-scans may also be used in alarm systems through comparison with predefined threshold data. Finally, raw signals and processed signals obtained during an imaging session may be exported from system 100 for data storage or additional evaluation.

In contrast to known ultrasonic holography systems, the ultrasonic holography imaging systems described herein are configured to generate and transmit non-homogeneous sound fields independent of transducer configuration. The ultrasonic holography imaging systems described herein enable the creation of real acoustic three dimensional images allowing the generation of a virtual image with improved definition and differentiation features, in comparison to known ultrasonic holography systems that work without the generation of a real acoustic image. In addition, the ultrasonic holography imaging systems described herein provide enhanced imaging that is capable of addressing the shape and configuration of the physical item being imaged. In addition, in contrast to known ultrasonic holography imaging systems, the systems and methods described herein provide for the creation of ultrasonic waveforms emitted from separate ultrasonic transceivers in an ultrasonic transducer array, such that at least two of the plurality of ultrasonic waveforms are differentiated from each other through variation of at least one of amplitude, frequency, and phase or modulations thereof.

Exemplary embodiments of a method for assembling an ultrasonic holography system and an ultrasonic holography system are described above in detail. The system and method are not limited to the specific embodiments described herein, but rather, steps of the methods and/or components of the systems may be utilized independently and separately from other steps and/or components described herein. For example, the systems and methods described herein may be used in combination with other measurement, monitoring and control systems, and are not limited to practice with only the components as described herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging system comprising:
   an ultrasonic transducer array including a plurality of transceiver elements configured to emit a plurality of ultrasonic waveforms toward a physical object, and receive a plurality of return ultrasonic waveforms reflected from the physical object, wherein the ultrasonic transducer array is configured to emit the plurality of ultrasonic waveforms to form an ultrasonic pulse field having a specific shape based at least in part on an array of points in space indicating target points for a plurality of ultrasonic waveforms corresponding to an image structure using pre-data stored in the memory device representing at least one of a shape of the physical object and a configuration of the physical object; and a processor system coupled to the ultrasonic transducer array, the processor system configured to:

generate a plurality of outgoing analog transceiver driving signals configured to cause the ultrasonic transducer array to emit the plurality of ultrasonic waveforms, wherein at least two of the plurality of ultrasonic waveforms as part of the ultrasonic pulse field are differentiated from each other through variation of at least one of amplitude and frequency;

receive a plurality of incoming analog waveform signals, generated by the ultrasonic transducer array, the incoming analog waveform signals representative of at least a portion of the plurality of return ultrasonic waveforms; and construct a virtual image, using the plurality of incoming analog waveform signals.

2. The system of claim 1, wherein the processor system comprises:

a digital processing portion configured to generate a plurality of digital waveform shaping signals corresponding to the plurality of analog transceiver driving signals, and wherein the digital processing portion is configured to process a plurality of incoming digital signals into the virtual image; and an analog processing portion coupled to the digital processing portion and to the ultrasonic transducer array, wherein the analog processing portion is configured to convert the plurality of digital waveform shaping signals into the plurality of outgoing analog transceiver driving signals for transmission to the ultrasonic transducer array and, and the digital processing portion is configured to convert the plurality of incoming analog waveform signals received from the ultrasonic transducer array into a plurality of incoming digital waveform signals.

3. The system of claim 2, wherein the analog processing portion comprises:

a plurality of digital-to-analog converters coupled to the digital processing portion configured to convert the plurality of digital waveform shaping signals received from the digital processing portion into the plurality of incoming analog waveform shaping signals; and a plurality of amplifiers coupled to corresponding ones of the plurality of digital-to-analog converters, the plurality of amplifiers further coupled to corresponding transceiver elements of the plurality of transceiver elements, wherein the plurality of transceiver elements are configured to convert the plurality of analog waveform shaping signals received from the plurality of digital-to-analog converters into the plurality of analog transceiver driving signals and transmitting the plurality of analog transceiver driving signals to corresponding ones of the plurality of transceiver elements.

4. The system of claim 3, wherein the digital processing unit comprises a waveform shaping section coupled to the plurality of digital-to-analog converters.

5. The system of claim 4, wherein the digital processing unit comprises a cycle control unit coupled to the waveform shaping section.

6. The system of claim 4, wherein the waveform shaping section is configured to generate digital waveform shaping signals configured to induce in a physical object one of the three following wave types: Lamb waves, Rayleigh waves, and creep waves.

7. The system of claim 2, wherein the analog processing portion comprises:

a plurality of amplifiers coupled to corresponding transceiver elements of the plurality of transceiver elements, wherein the plurality of amplifiers are configured to amplify the plurality of analog waveform signals received from the corresponding ones of the plurality of transceiver elements; and a plurality of analog-to-digital converters coupled to corresponding ones of the plurality of amplifiers, wherein the plurality of analog-to-digital converters are configured to convert the plurality of analog waveform signals received from the corresponding ones of the plurality of transceiver elements into a plurality of digital waveform signals.

8. The system of claim 7, wherein the digital processing unit comprises:

an image reconstruction unit coupled to the analog-to-digital converters, wherein the image reconstruction unit is configured to perform numerical reconstruction of the digital waveform signals towards converting the digital waveform signals into the virtual image; and at least one memory device coupled to the image reconstruction unit, wherein the at least one memory device is configured to store the digital waveform signals.

9. The system of claim 8, wherein the digital processing unit comprises at least one evaluation unit coupled to the image reconstruction unit wherein the at least one evaluation unit is configured to perform ultrasonic testing analysis on the virtual image.

10. The system of claim 7, wherein the analog processing portion comprises a plurality of filters, each filter coupled between an amplifier and a corresponding analog-to-digital converter.

11. A method for assembling an imaging system, the method comprising:

coupling a plurality of ultrasonic transceiver elements to form an ultrasonic transducer array, the plurality of transceiver elements configured to emit a plurality of ultrasonic waveforms toward a physical object; and coupling a processor system to the ultrasonic transducer array, the processor system configured to:

generate a plurality of outgoing analog transceiver driving signals configured to cause the ultrasonic transducer array to emit the plurality of ultrasonic waveforms, wherein at least two of the plurality of ultrasonic waveforms are differentiated from each other through variation of at least one of amplitude and frequency, wherein the plurality of ultrasonic waveforms forms an ultrasonic pulse field having a specific shape based at least in part on an array of points in space indicating target points for a plurality of ultrasonic waveforms corresponding to an image structure using pre-data stored in the memory device representing at least one of a shape of the physical object and a configuration of the physical object;

receive a plurality of incoming analog waveform signals, generated by the ultrasonic transducer array, the plurality of incoming analog waveform signals representative of at least a portion of the plurality of return ultrasonic waveforms; and construct a virtual image, using the plurality of incoming analog waveform signals.

12. The method of claim 11, the method comprising:
coupling a digital processing portion to an analog processing portion wherein the digital processing portion is configured to generate a plurality of digital waveform shaping signals corresponding to the plurality of analog transceiver driving signals, and wherein the digital processing portion is configured to process a plurality of incoming digital signals into the virtual image and analog processing portion is configured to convert the plurality of digital waveform shaping signals into the plurality of analog transceiver driving signals for transmission to the ultrasonic transducer array, and wherein the digital processing portion is configured to convert the incoming analog waveform signals received from the ultrasonic transducer array into a plurality of incoming digital signals; and
coupling the analog processing portion to the ultrasonic transducer array.

13. The method of claim 12, the method comprising:
coupling a plurality of digital-to-analog converters to the digital processing portion configured to convert the plurality of digital waveform shaping signals received from the digital processing portion into a plurality of analog waveform shaping signals; and
coupling a plurality of amplifiers to corresponding ones of the plurality of digital-to-analog converters; and
coupling the plurality of amplifiers to corresponding ones of the plurality of transceiver elements, wherein the plurality of transceiver elements are configured to convert the plurality of analog waveform shaping signals received from the plurality of digital-to-analog converters into the plurality of analog transceiver driving signals and to transmit the analog transceiver driving signals to corresponding ones of the plurality of transceiver elements.

14. The method of claim 13, the method further comprising coupling a waveform shaping section to the plurality of digital-to-analog converters.

15. The method of claim 14, the method further comprising configuring the waveform shaping section to generate digital waveform shaping signals configured to induce in a physical object one of the three following wave types: Lamb waves, Rayleigh waves, and creep waves.

16. The method of claim 12, the method further comprising:
coupling a plurality of amplifiers to corresponding ones of the plurality of transceiver elements, wherein the plurality of amplifiers are configured to amplify analog waveform signals received from the corresponding ones of the plurality of transceiver elements; and
coupling a plurality of analog-to-digital converters to corresponding ones of the plurality of amplifiers, wherein the plurality of analog-to-digital converters are configured to convert the analog waveform signals received from the corresponding ones of the plurality of transceiver elements into digital waveform signals.

17. The method of claim 16, the method further comprising:
coupling an image reconstruction unit to the analog-to-digital converters, wherein the image reconstruction unit is configured to perform numerical reconstruction of the plurality of digital waveform signals towards converting the plurality of digital waveform signals into the virtual image; and
coupling at least one memory device to the image reconstruction unit, wherein the at least one memory device is configured to store the plurality of digital waveform signals.

18. The method of claim 17, the method further comprising coupling at least one evaluation unit to the image reconstruction unit, wherein the at least one evaluation unit is configured to perform ultrasonic testing analysis on the virtual image.

19. A method for imaging a physical object, the method implemented using a processor system including a processing section coupled to a memory device, the method comprising:
defining an image structure using data stored in the memory device, the data representing a geometry of the physical object, wherein the defined image structure corresponds to an array of points in space as target points for a plurality of ultrasonic waveforms;
configuring an ultrasonic transducer array, the ultrasonic transducer array comprising a plurality of ultrasonic transceiver elements configured to emit the plurality of ultrasonic waveforms, wherein the configured ultrasonic transducer array forms an ultrasonic pulse field using the plurality of ultrasonic waveforms, wherein the ultrasonic pulse field has a specific shape based at least in part on the array of the points in space and at least one of a shape of the physical object and a configuration of the physical object derived from the data;
coupling the ultrasonic transducer array to the processing section and the memory device; and
storing, in the memory device, instructions executable by the processor system to cause the ultrasonic transducer array to emit the plurality of ultrasonic waveforms representative of the defined image structure, wherein at least two of the plurality of ultrasonic waveforms are differentiated from each other through variation of at least one of amplitude and frequency.

20. The method of claim 19, the method comprising:
emitting into the physical object, with the ultrasonic transducer array, a plurality of ultrasonic waveforms;
receiving, with the ultrasonic transducer a plurality of ultrasonic waveforms reflected from the physical object;
processing the plurality of reflected ultrasonic waveforms to produce a plurality of digital A-Scans; and
evaluating the plurality of digital A-scans.

\* \* \* \* \*